(12) United States Patent
Godara

(10) Patent No.: US 7,533,002 B2
(45) Date of Patent: May 12, 2009

(54) MEDICAL GENERATOR WITH ERROR LOGIC

(75) Inventor: Neil Godara, Mississauga (CA)

(73) Assignee: Baylis Medical Company Inc., Montreal (CA)

( * ) Notice: Subject to any disclaimer, the term of this patent is extended or adjusted under 35 U.S.C. 154(b) by 0 days.

(21) Appl. No.: 11/425,868

(22) Filed: Jun. 22, 2006

(65) Prior Publication Data

US 2007/0036271 A1 Feb. 15, 2007

Related U.S. Application Data

(63) Continuation of application No. 10/893,274, filed on Jul. 19, 2004, now Pat. No. 7,076,399.

(51) Int. Cl.
G06F 15/00 (2006.01)

(52) U.S. Cl. .................. 702/183; 702/185; 600/300; 607/17

(58) Field of Classification Search .......... 702/183, 702/185; 600/300, 508, 544, 547, 595, 587; 607/8, 17, 89, 67, 68, 48; 340/539.12, 573.1
See application file for complete search history.

(56) References Cited

U.S. PATENT DOCUMENTS

| | | | |
|---|---|---|---|
| 4,058,001 A | 11/1977 | Waxman | |
| 4,124,894 A | 11/1978 | Vick et al. | |
| 4,881,230 A | 11/1989 | Clark et al. | |
| 5,429,123 A | 7/1995 | Shaffer et al. | |
| 5,600,574 A | 2/1997 | Reitan | |
| 5,891,179 A * | 4/1999 | Er et al. | 607/27 |
| 5,914,875 A | 6/1999 | Monta et al. | |
| 6,421,554 B1 | 7/2002 | Lee et al. | |
| 6,438,408 B1 | 8/2002 | Mulligan et al. | |
| 6,565,562 B1 | 5/2003 | Shah et al. | |
| 6,788,965 B2 | 9/2004 | Ruchti et al. | |
| 7,127,376 B2 * | 10/2006 | Nashner | 702/185 |
| 2002/0115939 A1 | 8/2002 | Mulligan et al. | |
| 2003/0060692 A1 | 3/2003 | Ruchti et al. | |
| 2003/0074029 A1 | 4/2003 | Deno et al. | |
| 2003/0195774 A1 | 10/2003 | Abbo | |
| 2004/0039605 A1 | 2/2004 | Bardy | |
| 2004/0133119 A1 | 7/2004 | Osorio et al. | |
| 2004/0147969 A1 * | 7/2004 | Mann et al. | 607/17 |
| 2004/0167580 A1 * | 8/2004 | Mann et al. | 607/17 |
| 2004/0193068 A1 * | 9/2004 | Burton et al. | 600/544 |
| 2005/0027323 A1 | 2/2005 | Mulligan et al. | |
| 2005/0042681 A1 * | 2/2005 | Van Eyk et al. | 435/7.1 |
| 2005/0203497 A1 * | 9/2005 | Speeg et al. | 606/15 |
| 2005/0215914 A1 * | 9/2005 | Bornzin et al. | 600/508 |
| 2005/0278001 A1 * | 12/2005 | Qin et al. | 607/48 |
| 2006/0009810 A1 * | 1/2006 | Mann et al. | 607/17 |
| 2006/0059145 A1 * | 3/2006 | Henschke et al. | 707/6 |

OTHER PUBLICATIONS

Notice of Allowance for 1145-35, "Mailed on Feb. 14, 2006".

(Continued)

Primary Examiner—Carol S Tsai
(74) Attorney, Agent, or Firm—Dimock Stratton LLP

(57) ABSTRACT

A method and apparatus are disclosed for detecting, analyzing and displaying errors in a energy source of a medical treatment system. Detected errors are analyzed to define further errors. Errors may be classified, for example, in response to severity, and prioritized. Prioritization may depend on a scope of the error, an order of occurrence, importance, or other factors.

18 Claims, 2 Drawing Sheets

OTHER PUBLICATIONS

Ex Parte Quayle Action for 1145-35, "Mailed on Nov. 4, 2005".
Advisory Action for 1145-50, "Mailed on Jul. 11, 2008".
Final Action for 1145-50, "Mailed on Apr. 22, 2008".
Non Final Action for 1145-50, "Mailed on Oct. 17, 2007".

* cited by examiner

MEDICAL GENERATOR WITH ERROR LOGIC

TECHNICAL FIELD

The invention relates to medical generators, for example, for electrosurgical applications, and more particularly to controls for such generators.

BACKGROUND OF THE ART

Medical generators are widely used in medical treatment systems. Their numerous functions include: supplying energy for treatment, communicating with measuring, monitoring, and/or treatment devices, controlling the activity of one or more peripheral treatment devices (such as pumps or suction devices), computing and analyzing input data, and displaying or otherwise communicating treatment information to a user. With such a wide range of uses, medical generators often communicate with multiple devices, each of whose operational parameters may depend on the activity of other devices.

The complexity of multiple inputs and interactions, which gives medical generators their versatility and utility, can also cause more opportunities for errors to arise. These errors can often be difficult for a user to diagnose because of the multiple possible causes of a single problem. For example, in a medical treatment system that monitors impedance while energy is delivered to a tissue through a probe, an excessively high impedance measurement could be caused by vaporization of the tissue, a malfunctioning impedance monitor, or a disconnection of the treatment device.

It is often necessary to identify the causes of errors and to fix the errors as quickly as possible to ensure safety, due to the delicate nature of some medical treatment procedures. Frequently, however, individuals operating a medical treatment system do not have a technical background or a detailed knowledge of the way the system works. If there is an error in the operation of the medical treatment system, these users may not understand how to solve the error and may not recognize whether an error is signaling a more fundamental problem. Compounding this complexity are differences in component function with different modes of operation, meaning that one error may have different causes at different times.

Currently, some medical generators for use in medical treatment systems use a coded display requiring a user to look up an error code in documentation which may raise follow-up questions to help troubleshoot the problem further. This approach can be time consuming and inconvenient during a medical procedure. Some medical generators use an on-screen display that informs the operator of an error and may suggest possible courses of action. However, many errors, such as high impedance, may have a variety of possible causes and suggested courses of action for resolution. In these cases, it can be time consuming to determine which course of action will resolve the error. If multiple errors are detected additional time and effort will be required to determine whether the errors are jointly or independently caused, and which course(s) of action will optimally and efficiently resolve all errors.

U.S. Pat. No. 6,788,965, issued Sep. 7, 2004 to Ruchti et al, discloses a system for detecting errors and determining failure modes related to a non-invasive blood glucose monitor. Ruchti et al. disclose an error detection system that employs a hierarchical series of levels to determine whether or not a given glucose measurement is invalid. Each level utilizes different criteria (e.g. rudimentary specifications, patient history, etc.) for determining the validity of the measurement. Ruchti et al. do not describe a medical treatment apparatus with various functions, modes of operation or multiple inputs/outputs and do not describe an error logic system that may solve the difficulties associated with such an apparatus as described above.

A solution which addresses one or more of these shortcomings is desired.

SUMMARY OF THE INVENTION

There is provided a medical generator with error logic. In accordance with features of the present invention, errors are detected and diagnosed in a medical generator and/or its associated devices using error logic capable of detecting and classifying at least one error in the generator and/or an associated device.

Another aspect of the invention provides a generator for use in a medical treatment system, whereby the generator may be connected for operation with one or more associated devices and to receive measurements from said devices or from measuring devices. The generator comprises an error detecting unit capable of carrying out operations to detect at least one error in the generator and/or associated devices and to classify the error, as described using the method of the first aspect of the invention. The generator may comprise or be coupled to a display for displaying the at least one error.

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

Figure 1:
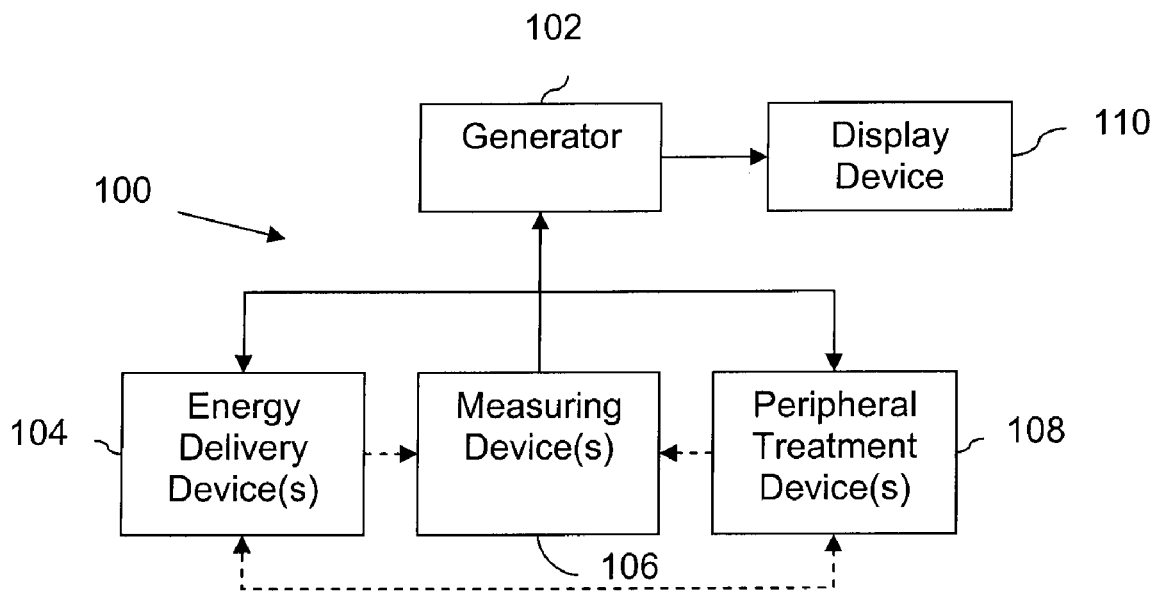
FIG. 1 illustrates a block diagram of an exemplary medical treatment system in which the present invention can be used.

A first embodiment of the invention provides a method of error detection and analysis to be used in an energy source, for example a generator, that supplies energy to a system 100 used to treat pain in an animal body, particularly a human (FIG. 1). The system 100 comprises a generator 102 for delivering energy through one or more energy delivery devices 104. Generator 102 may also control the activity of one or more peripheral treatment devices 108, such as pumps. Generator 102 can have many inputs, including measuring devices 106 (such as temperature and impedance monitors), inputs that relay information on the presence or type of attached devices (104 or 108) for example by using an integrated circuit. Attached devices 104 and 108 may be unconnected to one another, may communicate among each other or be connected to one another (for example, an energy-delivering probe having an internal channel to carry cooling fluid from a pump), and/or may be physically connected to the measuring device(s) 106 (for example, an energy delivering probe having a thermocouple mounted in the tip).

Figure 2:
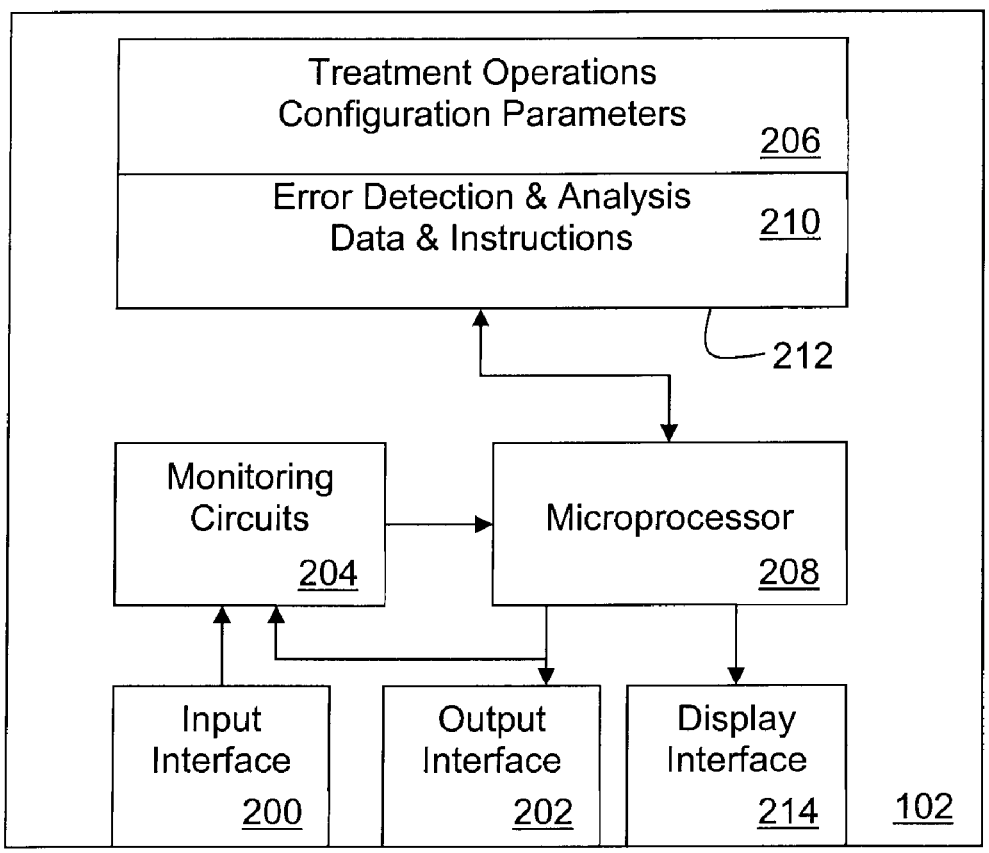
FIG. 2 illustrates a block diagram of the components of a generator in accordance with one embodiment of the invention.

FIG. 2 shows an illustrative embodiment of the components of generator 102. Generator 102 comprises an input interface 200 for receiving inputs from measuring devices 106 and, as applicable, attached devices 104 and 108. An output interface 202 supplies output for controlling or communicating with attached devices 104 and 108 and, as applicable, measurement devices 106. Monitoring circuits 204 monitor input received via input interface 200 (i.e. input measurements) and monitor output for supply via output interface 202 (i.e. output measurements). Information from the monitoring circuits 204 is communicated to an error detecting unit, such as a microprocessor 208, configurable by data and instructions 210 for error detection and analysis which may be stored in a memory 212. Configuration parameters 206 stored in memory 212 can also provide input to the microprocessor 208. Generator 102 further includes a display interface 214 for outputting a display of error information as further described below. Though shown as separate input and output interfaces, persons of skill in the art will appreciate that a combined input/output interface (I/O) may be employed. Though not shown, input interface 200, output interface 202 or an additional input, output or I/O interface may be coupled to one or more user input devices (keyboard, microphone, pointing device, scanner, etc.), storage devices, or communication networks for inputting, outputting or communicating data and commands for the operation of the generator, whether treatment operations or error detecting and analysis operations. While shown locally coupled to generator 102, memory 212 may be remotely located and coupled for communication with generator 102 via a suitable interface (not shown). Display interface 214 may couple generator 102 to a display device 110 (e.g. a monitor) or may comprise a communications interface to another system such as a computer system having a display device for receiving output of the display of the errors.

Figure 3:
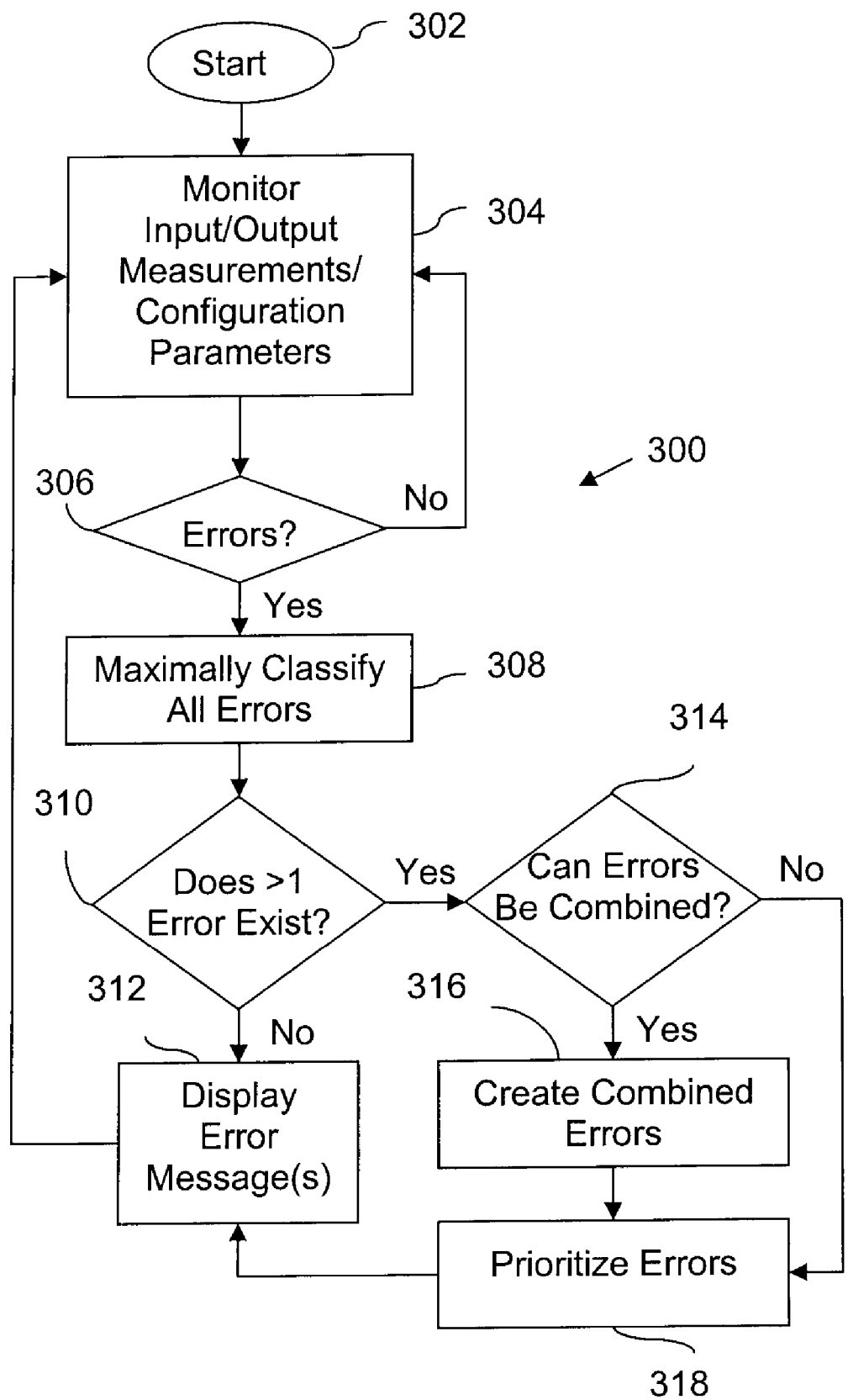
FIG. 3 illustrates a flow chart of operations for performing hierarchical error logic in accordance with an aspect of the invention.

FIG. 3 is a flowchart of operations 300 for error detection and analysis, according to a method aspect of the invention. In accordance with the preferred embodiment, operations 300 begin at start block 302, for example, following assembly of system 100 and power up. At step 304, input and output measurements are continuously monitored and measured values are compared to respective predefined threshold values or ranges of allowed values, on an ongoing basis. If a measurement is within a threshold or range, no error is generated at step 306 (No branch). When a measurement is beyond a threshold or outside a range, an error is generated (step 306, Yes branch). Errors can also be generated by comparing current system settings, or configuration parameters 206, to predefined values; for example, if it has been predefined that the system 100 must reach a set temperature and the total time for the treatment has been predefined, then an error will be generated if the preset time for the system 100 to reach the set temperature (ramp time) is greater than the total preset time for the treatment.

Multiple input and output measurements may be monitored allowing the generation of multiple errors at step 306 via Yes branch to step 308. Once an error is generated, operations 300 classify the error in response to specific conditions of the error. For example, if an invalid temperature measurement is detected, operations 300 may classify the temperature measurement as too low or too high. Many levels of increased specificity of classification may occur. For example, for a temperature measurement that is classified as too low: if the temperature measurement is between 5° C. and 15° C., the error classification may indicate a properly functioning device but a temperature too low to operate; if the temperature measurement is below 5° C., the error classification may indicate a malfunctioning temperature sensor. At step 308 errors will be classified to the maximum extent. An embodiment of a method of classification is discussed further herein below.

If at step 310 it is determined that only a single error exists, a detailed error message is displayed describing the error at step 312. Preferably, corrective action that can be taken to resolve the error is suggested. The display may use a natural language description of the error(s) and may include a suggested action to be taken by a user. In one alternate embodiment (not shown), the display of errors (step 312) is coincident with or precedes an automated modification of the operations of generator 102, such as the halting of energy delivery or switching to another mode based on the errors generated.

At step 310, if it is determined that multiple errors exist, operations 300 proceed via Yes branch to step 314. At this point, the set of errors is analyzed in order to determine whether any errors can be combined, being symptomatic of a particular problem. For example, simultaneous errors showing high impedance and an invalid temperature measurement may be indicative of a broken connector or disconnected device. In a preferred embodiment, the first detected errors are combined to form second errors, if applicable. The combination may be determined with reference to a predetermined lookup table or logic tree, discussed further below, which lists all possible first errors and the ways in which at least some of those first errors may be combined to form new (i.e. second) errors. If at least some of these first errors can be combined (step 314, Yes branch), such first errors are combined to form second errors (step 316). Any remaining uncombined first errors remain as independent errors (step 314, No branch). All second (i.e. combined) errors and remaining first (i.e. independent) errors are preferably prioritized (step 318). At step 312, first and second errors can be displayed one at a time, or can be displayed in a number of other ways including simultaneously, with all errors appearing at once, in groups, or on separate screens that can be toggled or scrolled.

In the preferred embodiment, prioritization of first and second errors 318 is responsive to the degree of complexity of resolving each error, or degree to which resolving one error will resolve other concomitant errors. For example, an error that requires an entire treatment device to be changed is prioritized over an error that requires repositioning a device and not changing the device. However, prioritization of errors may also be based on a number of other factors such as, the measurable parameter to which the error relates, the order in which the error was detected, or any other characteristic by which errors can be sorted.

Grouping and prioritizing errors may aid a user in resolving system problems quickly and with minimal confusion, which can help ensure patient safety by reducing treatment disruption as both error diagnosis and correction times are minimized. For example, as may occur with a prior art device, a user may receive two concurrent errors showing high impedance and invalid temperature measurement with no indication of what is causing the errors. In such a case, the user would have to check all possible sources of each error, to determine the actual cause(s) of the errors, and to determine whether each error was caused by a problem with the equipment or by a potentially dangerous problem with the treatment itself (e.g. high impedance being caused by tissue vaporization). Knowing if the actual cause of both errors is simply that a device has become disconnected, will allow the user to quickly resolve the problem and continue with the treatment, in accordance with a goal of the present invention.

While FIG. 3 shows a general flowchart of operations for analyzing and clarifying errors, the criteria by which errors are defined can vary in a number of ways. In the preferred embodiment, the sets or ranges of acceptable output or input measurements, or the thresholds above or below which errors are triggered, such as ranges of temperature, can be changed, or may be made dependent on the values of other measured parameters. As well, in the preferred embodiment, a mode of operation or progress through a treatment procedure, can affect the classification of errors.

In one embodiment, three different types of errors (e.g. type 1, type 2 and type 3) may be produced depending on the mode of operation or procedural progress. The operation of the generator 102 may be responsive to the type of error produced. Type 1 errors are generated when immediate patient and/or equipment protection is required. For a type 1 error, treatment operations of the system 100 may be automatically modified, discontinuing all generator output to energy delivery devices 104 and/or peripheral treatment devices 108. Further treatment using the system 100 requires a system reset. Type 1 errors cannot be immediately resolved by the user and have the highest priority.

Unlike a type 1 error, type 2 errors are anticipated to be correctable by the user and treatment may progress once they have been resolved. Generator 102 may respond to a type 2 error by modifying the operation of the system 100 either discontinuing all generator output 202 to energy delivery devices 104 and/or peripheral treatment devices 108 or switching the operation of the system 100 to a predetermined mode of operation dependent on the error. The errors remain displayed until the problem(s) that cause them is (are) resolved.

Type 3 errors have the lowest priority of the three types of errors; treatment operations of the system 100 need not be automatically halted or suspended by generator 102 and clear after being briefly displayed, or upon being cleared manually by the user. Whether a given error is classified as a type 1, 2, or 3 error depends on the current mode of operation. For example, an invalid impedance measurement in a standby mode may be due to a reasonable action by the user, such as a removal of a probe in order to inject additional treatment fluid through the introducer needle, but the same invalid impedance measurement in an energy delivery mode could indicate vaporization of body tissue or faulty equipment.

Another factor that can affect the classification of errors is the configuration parameters 206 within generator 102. In the preferred embodiment, generator 102 can be configured to expect a certain number or type of device(s) to be connected to it, and can generate errors based on this expectation. For example, if generator 102 is configured to apply radiofrequency energy through one probe, and two probes are connected, an error will be displayed in order to inform the user of excess connections, even if the probe through which energy will be delivered is working correctly.

While the embodiment discussed above describes a system 100 capable of analyzing errors as they occur, based on predetermined criteria, it is also possible that such a system 100 could include analysis of trends in measurements in order to detect errors (for example, producing an error if the temperature drops 10° C. in 1 second, rather than only producing an error if the temperature apparently instantaneously drops below a certain level), or that such a system 100 could detect errors based on analysis of trends in errors (for example, repeated high impedance errors in a given mode, occurring with greater frequency than could be attributed to user actions, can indicate a frayed wire). Trend analysis can also be used to create type 3 errors, or warnings of imminent errors. For example, if repeated high temperature errors were to be generated, a type 3 error could be produced to warn the user that they are in danger of causing permanent damage to the system 100 (type 1 error imminent). In one embodiment, ranges of acceptable input data for error determination are dependent on trend analysis of errors; for example, if repeated errors are generated based on a certain measurable parameter, the sensitivity of measurement of that parameter could be automatically adjusted (increased or decreased).

Table 1 shows a portion of a logic tree as used in one embodiment for the classification of errors in a lesion-making system 100. In this example, the lesion-making system 100 comprises a generator 102, up to two probes 104 each furnished with electrodes (i.e. one active electrode and one return electrode) for the delivery of energy, measuring devices including a thermocouple and an impedance monitor 106, and may comprise a grounding pad to be used to the receive the delivered energy. In the example of Table 1, the system 100 is configured to deliver energy through only one probe 104, and is in "READY" mode, prior to the delivery of energy.

TABLE 1

LESIONING (READY) (Secondary Probe disabled)

CHECK 1 Primary Probe Thermocouple temperature valid?
Result    Pass                                      Fail
Action    Goto CHECK 3                              Goto CHECK 2
CHECK 2 Valid Impedance between RF Active and RF Return?
Result    Pass                                      Fail
Action    E01                                       E02
CHECK 3 Secondary Probe Thermocouple temperature not present?
Result    Pass                                      Fail
Action    Goto CHECK 4                              W11
CHECK 4 Valid Impedance between RF Active and RF Return?
Result    Pass                                      Fail
Action    Goto LESIONING ON - INITIALIZATION        If High: W12
          (Secondary Probe disabled)                If Low: W13

Consider, as an example, a system configured according to Table 1, whereby a thermocouple 106 mounted on probe 104 was not functioning. In this example, CHECK 1 would find the Primary Probe Thermocouple temperature to be invalid and fail, moving to CHECK 2. If the impedance measurement was valid, CHECK 2 would pass and error E01 would be displayed informing the user of a temperature error. Table 2 lists a portion of the display messages for system 100 of the present embodiment. If, in a contrasting example, the probe 104 was properly connected, but was not in contact with the tissue, CHECK 1 would find the Primary Probe Thermocouple temperature to be valid and pass to CHECK 3. CHECK 3 would find no indication of the presence of a second probe 104 and pass to CHECK 4. CHECK 4 would find an invalid impedance between the two probes 104 and fail, creating an error. The invalid impedance error would further be classified as a high impedance error, causing error W12 (see Table 2) to be displayed. If, in the system 100 used in the above examples, a probe 104 were disconnected, both invalid temperature and high impedance errors would result. In this example, CHECK 1 would find the Primary Probe Thermocouple temperature to be invalid and proceed to CHECK 2. CHECK 2 would then find the impedance to be invalid and would fail, displaying error E02, as described in Table 2, which informs the user that the probe 104 is not connected. Thus, rather than displaying separate errors for invalid temperature and high impedance, the invention produces a third, unique, combined error.

TABLE 2

| Type | Code | Displayed Message |
|------|------|-------------------|
| TYPE 2 | E01 | Invalid Temperature Reading<br>Check Probe and Cable Connections Possible defective probe or cable. Try new probe and cable if problem persists |
| TYPE 2 | E02 | Probe Not Connected<br>Check probe and cable connections. Probe or cable(s) may be defective |
| TYPE 2 | E03 | Temperature Out-of-range<br>Outside 15-100° C. expected range. Probe or cable may be defective |
| TYPE 2 | E04 | Secondary Probe Connected But Disabled in Advance Settings<br>Disconnect Secondary Probe or, if desired, enable Secondary Probe in ADVANCED SETTINGS |
| TYPE 2 | E05 | High Impedance Detected<br>Check Probe and Cable Connections. Probe or Cable may be defective |
| TYPE 2 | E06 | Low Impedance Detected<br>Check probe and cable connections. Possible short circuit in probe or cable |
| TYPE 3 | W11 | Secondary Probe Connected But Disabled in Advance Settings<br>Disconnect Secondary Probe or, if desired, enable Secondary Probe in ADVANCED SETTINGS |
| TYPE 3 | W12 | High Impedance Detected<br>Check Probe and Cable Connections. Probe or Cable may be defective |
| TYPE 3 | W13 | Low Impedance Detected<br>Check probe and cable connections. Possible short circuit in probe or cable |

Table 3 provides a manner to classify errors for a system 100 configured to deliver energy through only one probe 104, similar to Table 1, which is in "ON" (energy delivery) mode. As described above, a system 100 may be configured to have different thresholds above or below which errors are detected, depending on operating modes, or could classify errors differently depending on a current operating mode. For example, in a system 100 configured according to Table 3, if a probe 104 is properly connected but is not in contact with the tissue while energy is delivered, CHECK 1 would find the Primary Probe Thermocouple temperature to be valid and pass to CHECK 3. CHECK 3 would find no valid measurement to indicate the presence of a second probe 104 and pass to CHECK 4. CHECK 4 would find an invalid impedance and fail, creating an error. The invalid impedance error would further be classified as a high impedance error, causing error E05, as shown in Table 2, to be displayed. Unlike error W12 in the above example, which corresponds to a Type 3 error, and would display on the generator screen for a number of seconds, but would not modify the treatment operations of the system 100, error E05 is a Type 2 error and generator 102 will respond to modify its operations to halt treatment operations (i.e. discontinuing the delivery of energy). Thus, the type of error can depend on a mode of operation of the generator.

TABLE 3

LESIONING ON (Secondary Probe disabled)

| CHECK 1 Primary Probe Thermocouple temperature valid? | |
|---|---|
| Result | Pass | Fail |
| Action | Goto CHECK 3 | Goto CHECK 2 |
| CHECK 2 Valid Impedance between RF Active and RF Return? | |
| Result | Pass | Fail |
| Action | E03 | E02 |
| CHECK 3 Secondary Probe Thermocouple temperature not present? | |
| Result | Pass | Fail |
| Action | Goto CHECK 4 | E04 |

TABLE 3-continued

LESIONING ON (Secondary Probe disabled)

| CHECK 4 Valid Impedance between RF Active and RF Return? | |
|---|---|
| Result | Pass | Fail |
| Action | Goto LESIONING DONE (Secondary Probe disabled) | If High: E05<br>If Low: E06 |

Tables 1 and 3 show a portion of logical configuration data for detecting and analysing errors based on a physical configuration of the system 100. For example, if a system 100 were configured to deliver energy through only one probe 104, as in Table 1, but had 2 probes 104 connected, the system 100 would find the Primary Probe Thermocouple temperature to be valid and pass to CHECK 3. CHECK 3 would then detect the presence of a valid temperature reading from the thermocouple 106 attached to the second probe 104 and would fail, displaying error W11, which instructs the user to either remove the second probe 104, if it is not intended to be used, or to enable the use of the second probe 104 (Table 2).

Variations to the embodiments and examples described above include, but are not limited to: types of inputs or outputs, the language or classification (e.g. a numbering system) used in the display of error messages, the manner of communicating errors (including displaying the messages, or communicating the errors to other devices for displaying and/or other use), the criteria for combining errors, the classification of types or degrees of error, and/or the specific physical configuration of a medical treatment system using such an error logic, may be employed by any user that is skilled in the art, and are intended to be included within the scope of the invention. The scope of the invention is therefore intended to be limited solely by the scope of the appended claims.

I claim:

1. A method of classifying errors in a medical treatment system comprising an energy source having a plurality of modes of operation and at least one associated device, the method comprising the steps of:
   detecting at least one error in the operation of at least one of the energy source and the at least one associated device; and
   assigning a classification to the at least one error to determine a response of the energy source to the at least one error, the classification being dependent upon a current mode of operation in which the energy source is being operated when the at least one error is detected, such that the at least one error would be assigned a different classification if detected in at least one of the plurality of modes of operation other than the current mode of operation.

2. The method of claim 1, wherein the step of detecting at least one error comprises the sub-step of:
   comparing at least one of input measurements, output measurements, and configuration parameters for the operation of the energy source and the at least one associated device, with respective expected measurements and expected parameters.

3. The method of claim 2, wherein at least some of the expected measurements and expected parameters are responsive to manual changing.

4. The method of claim 2, wherein at least some of the expected measurements and expected parameters are responsive to the current mode of operation of the energy source.

5. The method of claim 2, wherein at least some of the expected measurements and expected parameters are responsive to measurements input into the system.

6. The method of claim 2, wherein at least some of the expected measurements and expected parameters are responsive to the at least one error.

7. The method of claim 2, wherein the step of assigning a classification comprises classifying the at least one error in response to specific values of the input measurements, output measurements, and configuration parameters used in the detection of the at least one error.

8. The method of claim 1, further comprising a step of outputting a display of at least one of the at least one classified errors.

9. The method of claim 1, wherein the step of assigning a classification comprises classifying the at least one error based on a severity of the at least one error.

10. The method of claim 1, wherein the plurality of modes of operation comprises at least one energy delivery mode and at least one mode in which energy is substantially not delivered, and whereby an error detected during the energy delivery mode is assigned a classification different than the classification assigned to the same error when detected in the mode in which energy is substantially not delivered.

11. The method of claim 1, wherein the medical treatment system is used in a treatment procedure, and wherein the classification of the at least one error is responsive to progression through the treatment procedure.

12. The method of claim 1, wherein the at least one error comprises at least two errors, and wherein two or more of the at least two errors are substantially identical and wherein one of the two or more substantially identical errors is detected while the energy source is in a first mode of operation and another of the two or more substantially identical errors is detected while the energy source is in a second mode of operation.

13. The method of claim 1, further comprising a step of responding to the at least one error, wherein the response to the at least one error is at least partially dependent on the classification of the at least one error.

14. An energy source for delivering energy to at least one associated device, the energy source having a plurality of modes of operation and comprising an error detecting unit for:
    detecting at least one error in the operation of at least one of the energy source and the at least one associated device; and
    assigning a classification to the at least one error to determine a response of the energy source to the at least one error, the classification being dependent upon a current mode of operation in which the energy source is being operated when the at least one error is detected such that the at least one error would be assigned a different classification if detected in at least one of the plurality of modes of operation other than the current mode of operation.

15. The energy source of claim 14, wherein the error detecting unit compares at least one of input measurements, output measurements, and configuration parameters for the operation of the energy source and the at least one associated device, with respective expected measurements and expected parameters.

16. The energy source of claim 14, wherein the error detecting unit is operable to classify the at least one error based on a severity of the at least one error.

17. The energy source of claim 14, wherein the error detecting unit comprises a processor.

18. The energy source of claim 17, wherein the error detecting unit comprises a microprocessor.

* * * * *